(12) United States Patent
Bavaro et al.

(10) Patent No.: US 7,833,597 B2
(45) Date of Patent: *Nov. 16, 2010

(54) POLYMERIC MARKER WITH HIGH RADIOPACITY FOR USE IN MEDICAL DEVICES

(75) Inventors: Vincent Peter Bavaro, Temecula, CA (US); John Arthur Simpson, Carlsbad, CA (US); Peter D'Aquanni, Murrieta, CA (US); Aaron Baldwin, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 306 days.

This patent is subject to a terminal disclaimer.

(21) Appl. No.: 11/877,905

(22) Filed: Oct. 24, 2007

(65) Prior Publication Data

US 2008/0065010 A1    Mar. 13, 2008

Related U.S. Application Data

(60) Division of application No. 10/945,637, filed on Sep. 21, 2004, now Pat. No. 7,303,798, which is a continuation-in-part of application No. 10/667,710, filed on Sep. 22, 2003, now abandoned.

(51) Int. Cl.
  *B29C 47/00*   (2006.01)
  *A61M 31/00*   (2006.01)
  *A61B 5/05*    (2006.01)

(52) U.S. Cl. .................. 428/36.9; 428/36.4; 604/103.1; 600/424

(58) Field of Classification Search ..................... 604/19
See application file for complete search history.

(56) References Cited

U.S. PATENT DOCUMENTS

| 3,605,750 | A | 9/1971 | Sheridan et al. |
| 3,618,614 | A | 11/1971 | Flynn |
| 4,571,240 | A | 2/1986 | Samson et al. |
| 4,581,390 | A | 4/1986 | Flynn |
| 4,588,399 | A | 5/1986 | Nebergall et al. |
| 4,714,721 | A | 12/1987 | Frank et al. |
| 4,796,637 | A | 1/1989 | Mascuch et al. |
| 4,921,483 | A | 5/1990 | Wijay et al. |
| 4,935,019 | A | 6/1990 | Papp, Jr. |

(Continued)

FOREIGN PATENT DOCUMENTS

EP      0203833 A1    12/1986

(Continued)

*Primary Examiner*—Nicholas D Lucchesi
*Assistant Examiner*—Pritesh Patel
(74) *Attorney, Agent, or Firm*—Fulwider Patton LLP

(57) ABSTRACT

High radiopacity is achieved in a polymeric marker by combining a polymeric resin, a powdered radiopaque agent having uniformly shaped particles of a specific particle size distribution and a wetting agent. The method to produce the marker calls for the blending and pelletization of these materials followed by extrusion onto support beading. The resulting supported tubing is subsequently cut to length with the beading still in place. After ejection of the beading remnant the marker is slipped into place on the device to be marked and attached by melt bonding. Marking of a guidewire allows lesions to be measured while the marking of balloon catheters allow the balloon to be properly positioned relative to a lesion.

4 Claims, 1 Drawing Sheet

U.S. PATENT DOCUMENTS

| | | | |
|---|---|---|---|
| 4,938,220 A | 7/1990 | Mueller, Jr. | |
| 4,946,466 A | 8/1990 | Pinchuk et al. | |
| 4,990,138 A | 2/1991 | Bacich et al. | |
| 5,045,071 A | 9/1991 | McCormick et al. | |
| 5,300,048 A | 4/1994 | Drewes, Jr. et al. | |
| 5,409,006 A | 4/1995 | Buchholtz et al. | |
| 5,429,617 A | 7/1995 | Hammersmark et al. | |
| 5,499,973 A | 3/1996 | Saab | |
| 5,549,552 A | 8/1996 | Peters et al. | |
| 5,554,121 A | 9/1996 | Ainsworth et al. | |
| 5,667,767 A | 9/1997 | Greff et al. | |
| 5,693,015 A | 12/1997 | Walker et al. | |
| 5,709,658 A | 1/1998 | Sirhan et al. | |
| 5,743,875 A | 4/1998 | Sirhan et al. | |
| 5,769,868 A | 6/1998 | Yock | |
| 5,776,141 A | 7/1998 | Klein et al. | |
| 5,807,355 A | 9/1998 | Ramzipoor et al. | |
| 5,827,312 A | 10/1998 | Brown et al. | |
| 5,846,199 A | 12/1998 | Hijkema et al. | |
| 6,036,682 A | 3/2000 | Lange et al. | |
| 6,164,283 A | 12/2000 | Lesh | |
| 6,179,811 B1 | 1/2001 | Fuguso et al. | |
| 6,340,367 B1 | 1/2002 | Stinson et al. | |
| 6,355,058 B1 | 3/2002 | Pacetti et al. | |
| 6,428,512 B1 | 8/2002 | Anderson et al. | |
| 6,436,056 B1 | 8/2002 | Wang et al. | |
| 6,540,721 B1 | 4/2003 | Voyles et al. | |
| 6,626,936 B2 | 9/2003 | Stinson | |
| 7,303,798 B2 * | 12/2007 | Bavaro et al. | 428/36.9 |
| 2001/0012968 A1 | 8/2001 | Preissman | |
| 2003/0088195 A1 | 5/2003 | Vardi et al. | |
| 2004/0220549 A1 | 11/2004 | Dittman et al. | |
| 2005/0064223 A1 | 3/2005 | Bavaro et al. | |

FOREIGN PATENT DOCUMENTS

| | | |
|---|---|---|
| EP | 0203833 B1 | 12/1986 |
| EP | 0938879 A2 | 9/1999 |
| EP | 0938879 A3 | 9/1999 |
| EP | 0987042 A2 | 9/1999 |
| EP | 0987042 A3 | 9/1999 |
| JP | 07-501331 | 2/1995 |
| WO | 93/10440 A1 | 5/1993 |
| WO | 9310440 A1 | 5/1993 |
| WO | 0240077 A2 | 5/2002 |
| WO | 0240077 A3 | 5/2002 |
| WO | 02096474 A1 | 12/2002 |
| WO | 03089012 A2 | 10/2003 |
| WO | 03089012 A3 | 10/2003 |
| WO | 03101343 A1 | 12/2003 |

* cited by examiner

POLYMERIC MARKER WITH HIGH RADIOPACITY FOR USE IN MEDICAL DEVICES

CROSS-REFERENCES TO RELATED APPLICATION

This application is a division of currently U.S. patent application Ser. No. 10/945,637 filed Sep. 21, 2004, now U.S. Pat. No. 7,303,798 which is a continuation-in-part of application Ser. No. 10/667,710, filed Sep. 22, 2003, now abandoned.

BACKGROUND OF THE INVENTION

The present invention is directed to elongated intracorporeal devices, and more particularly intraluminal devices for stent deployment, percutaneous transluminal coronary angioplasty (PTCA), and the similar procedures. PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and increase the blood flow through the artery. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced therein until the preshaped distal tip of the guiding catheter is disposed within the aorta adjacent the ostium of the desired coronary artery. A balloon dilatation catheter may then be advanced through the guiding catheter into the patient's coronary artery until the balloon on the catheter is disposed within the stenotic region of the patient's artery.

Once properly positioned across the stenosis, the balloon is inflated one or more times to a predetermined size with radiopaque liquid at relatively high pressures (e.g., generally 4-12 atmospheres) to dilate the stenosed region of a diseased artery. After the inflations, the balloon is finally deflated so that the dilatation catheter can be removed from the dilatated stenosis to resume blood flow.

Similarly, balloon catheters may be used to deploy endoprosthetic devices such as stents. Stents are generally cylindrical shaped intravascular devices that are placed within a damaged artery to hold it open. The device can be used to prevent restenosis and to maintain the patency of blood vessel immediately after intravascular treatments. Typically, a compressed or otherwise reduced diameter stent is disposed about an expandable member such as a balloon on the distal end of the catheter, and the catheter and stent thereon are advanced through the patient's vascular system. Inflation of the balloon expands the stent within the blood vessel. Subsequent deflation of the balloon allows the catheter to be withdrawn, leaving the expanded stent within the blood vessel.

Typically, the distal section of a balloon catheter or other percutaneous device will have one or more radiopaque markers in order for the operator of the device to ascertain its position and orientation under X-ray or fluoroscopy imaging. Generally, a band or ring of solid radiopaque metal is secured about an inner or outer shaft of a balloon catheter to serve as a radiopaque marker. Such configuration, however, locally stiffens the catheter shaft and thereby imparts an undesirable discontinuity thereto as the solid metal bands are relatively inflexible compared to a polymer balloon catheter shaft. Additionally, the metallic markers are relatively expensive to manufacture and relatively difficult to positively affix to an underlying device.

As is described in U.S. Pat. No. 6,540,721, which is incorporated herein by reference, many of the problems associated with the use of conventional markers may be overcome by replacing the rigid precious metal tubing with a polymer that is filled or doped with a suitable radiopaque agent. Such marker may be formed by blending a polymer resin with a powdered, radiographically dense material such as elemental tungsten and then extruding the composition to form a tubular structure with an appropriate inner diameter and wall thickness. The extrusion may then be cut to discrete lengths and installed onto the intended component via a melt bonding process.

A shortcoming of such an approach has been found to be the apparent limit to which a suitable polymer can be filled with a radiographically dense material to yield a composition that can be successfully compounded, economically shaped into suitable dimensions for markers and easily assembled onto a component without unduly compromising the desirable properties of the polymer matrix. The fill ratio that is achievable will determine how thick a marker must be in order to achieve a particular degree of radiopacity. In the case of tungsten in a polymer such as Pebax (polyether block amide), the fill ratio limit has heretofore been found to be about 80 weight percent. Such weight percentage equates to about 18 volume percent which requires the marker to be excessively thick in order to achieve adequate radiopacity.

A polymeric marker is therefore needed having a substantially higher fill ratio than has heretofore been possible. Such marker would allow devices to be rendered highly visible without an inordinate increase in overall profile nor a compromise of the flexibility of the underlying component.

SUMMARY OF THE INVENTION

The invention is directed to a polymeric radiopaque marker for a medical device.

The present invention overcomes the shortcomings of previously described polymeric radiopaque markers by enabling a polymer to be filled or doped with a considerably greater quantity of a radiopaque agent than has heretofore been achievable. The increased fill ratio nonetheless allows uniform pellets to be compounded and an extrusion with the appropriate wall thickness to be formed. The resulting marker provides an unprecedented combination of radiopacity and flexibility. Such marker would allow any of various intraluminal devices to be radiopaquely marked including, but not limited to, coronary and peripheral balloon catheters, stent delivery catheters, and guiding catheters as well as guidewires.

The marker of the present invention relies on the use of radiopaque materials with a preselected particle shape and a preselected particle size distribution as well as the inclusion of one or more additives in the polymer/radiopaque agent blend. A multifunctional polymeric additive is added to the composition in order to enhance the wetting, adhesive and flow properties of the individual radiopaque particles by the polymer so as to cause each particle to be encapsulated by the polymer and thereby allow the polymer to form a continuous binder. An antioxidant may optionally be added in order to preserve the high molecular weight of the polymer matrix as it is exposed to the high temperatures and shear stresses associated with the compounding and extrusion processes.

While previous attempts to increase fill ratios have involved tungsten powder of relatively fine particle size, the present invention relies on the use of particles of increased size in order to achieve such end. An increase in particle size has been found to allow the polymer to more effectively function as a continuous binder and thereby increase ductility at a given fill ratio or maintain ductility at increased fill ratios. It has been found that in constraining the average particle size to at least 2 microns and limiting maximum particle size to about 20 microns provides the desired results. In the case of tungsten in Pebax, a fill ratio of about 91.3 weight percent (equivalent to 36.4 volume percent) or more is readily attainable for a polymeric marker formed in accordance with the invention. In one embodiment, the fill ratio is about 90.8 weight percent (34.9 volume percent) to about 93.2 weight percent (42.7 volume percent). Additionally, it has been found that the process by which the tungsten powder is produced has a considerable effect on both particle size distribution as well as the shape of the individual particles. Tungsten powder produced by either a "pusher" process or "atomization" process, then milled and classified has been found to provide discrete particles having a more equiaxed shape and size respectively and are therefore more ideally suited for the purposes of the present invention than powders produced employing a "rotary" process.

The marker of the present invention is manufactured by first tumble mixing the polymer resin with a pelletized wetting agent, such as maleic anhydride graft polyolefin resin (MA-g-PO), and an antioxidant and then introducing the mixture into the primary feeder of a twin screw extruder. The mixture is fed in at a controlled mass flow rate and conveyed down the barrel length as it is heated above its melting temperature and blended. At a point downstream, tungsten powder is introduced into the mix at a controlled mass flow rate via a secondary feeder. The tungsten powder and the molten ingredients become intimately intermixed as they are conveyed downstream and discharged through a die as molten strands which are cooled in water and subsequently pelletized. The markers are subsequently formed by extruding the tungsten filled polymer onto a continuous beading of PTFE, and drawn down to yield the desired wall thickness. The extrusion tolerances are such that the outer diameter of the extrusion can vary by as much as 0.001 inch, which is large enough to significantly affect the radiopacity and profile of the finished marker. Consequently, in a presently preferred embodiment, the extrusion is hot die necked (i.e., the extruded tube on a support mandrel, such as the PTFE beading, is pulled through a heated die to take on the die size), to resize the outer diameter and provide the desired wall thickness. The extrusion is then cut to the desired lengths, preferably with the beading still in place so as to provide support. Removal of the beading remnant then allows the marker to be slipped onto the medical device or component thereof to be marked and melt bonded in place. The polymeric marker is typically a closed, solid-walled band with a tubular or annular shape. However, the polymeric marker can have a variety of suitable shapes. Reliance on melt bonding obviates the need for the marker to completely surround the underlying device. Markers can for example be longitudinally split in half to form two markers of C-shaped cross-section. Or, solid strands of extruded marker material may be melt bonded to one side to form one or more longitudinal stripes or helical patterns.

During melt bonding, the polymeric marker is heated to an elevated temperature sufficient to melt the polymeric material to produce the melt bond. However, in one presently preferred embodiment, the elevated temperature is low enough to minimize or prevent flowing of the polymeric material of the marker. Consequently, the double wall thickness (inner diameter minus outer diameter) of the polymeric marker after melt bonding is equal to or not substantially less than (i.e., not more than about 5 to about 25% less than) the double wall thickness prior to melt bonding. Although some rounding of the edges of the polymeric marker may occur during melt bonding, the maximum wall thickness of the polymeric marker is preferably not reduced during the melt bonding. The marker radiopacity is strongly affected by both the percent loading of radiopaque material and the final wall thickness of the marker. Consequently, the percent loading of radiopaque material and the wall thickness of the finished marker are carefully controlled to provide the desired radiopacity. If the wall thickness of the polymeric marker is less than the required minimum wall thickness, the radiopacity of the marker will be too low. On the other hand, if the outer diameter/wall thickness of the polymeric marker is greater than the required maximum outer diameter/wall thickness, the large profile and added stiffness of the marker will disadvantageously affect catheter performance. Thus, the hot die necked extrusion has an outer diameter and wall thickness which is within the minimum and maximum desired values, so that little or no thinning of the marker is required during melt bonding of the marker to provide the desired outer diameter. As a result, a decrease in wall thickness which can reduce the radiopacity of the finished marker is prevented or minimized during bonding. In one embodiment, the polymeric marker is adhesively bonded to the medical device or component, and as a result, the wall thickness of the marker is not affected by the bonding process.

Due to its high radiopacity, flexibility and melt bondability, the marker of the present invention is readily attached to for example the inner member of a balloon catheter, a guidewire, and even a guide catheter tip. The attachment of radiopaque markers of known dimensions to a guidewire or the attachment to a guidewire of multiple radiopaque markers with known separation distances impart a measurement capability to the catheter that allows a physician to quickly and easily measure lesions and decide on appropriate stent lengths.

These and other features of the present invention will become apparent from the following detailed description of preferred embodiments which, taken in conjunction with the accompanying drawings, illustrate by way of example the principles of the present invention.

DETAILED DESCRIPTION OF THE PREFERRED EMBODIMENTS

Figure 1:
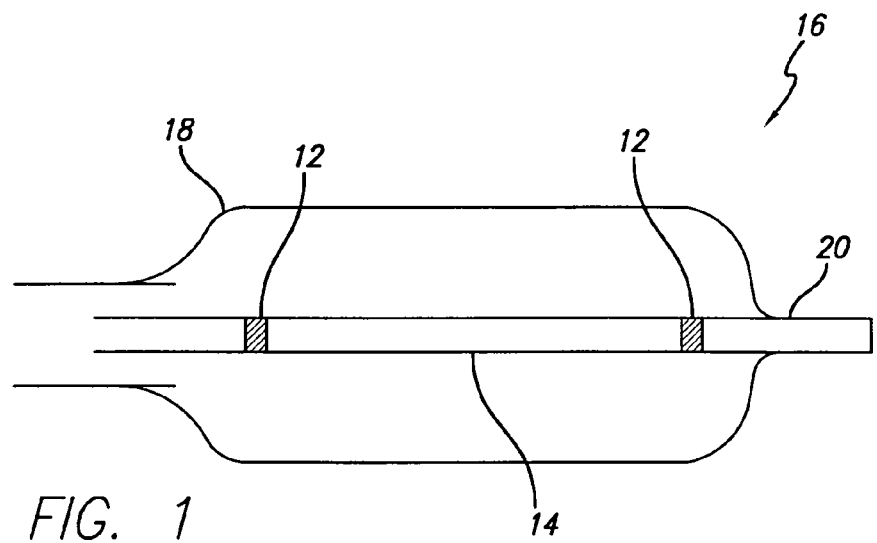
FIG. 1 is an enlarged side view of the radiopaque markers of the present invention attached to a balloon catheter.

The present invention provides a radiopaque marker for use on a variety of devices that is flexible, highly radiopaque and is easily attachable to such devices by melt bonding. These properties allow markers to be of minimal thickness and thereby minimize the effect the marker has on the overall profile and stiffness of the device to which it is to be attached.

In order to achieve the high fill ratios that are necessary to attain the desired radiopacity and in order to do so without compromising the compoundability and workability of the polymeric material nor its ultimate strength and flexibility, a number of different parameters have been found to be of importance. More specifically, both the particle shape and particle size of the radiopaque agent must be carefully controlled while the inclusion of a wetting agent such as MA-g-PO in the polymer blend is critical. An antioxidant may additionally be included in an effort to reduce the adverse effect the high processing temperatures and shear stresses may have on polymer properties.

A number of polymeric materials are well suited for use in the manufacture of the markers of the present invention. The material preferably comprises a low durometer polymer in order to render the marker sufficiently flexible so as not to impair the flexibility of the underlying medical device component to which the finished marker is to be attached. Additionally, in one embodiment, the polymer is preferably compatible with the polymeric material of which the component is constructed so as to allow the marker to be melt bonded in place. For example, in one embodiment, the polymeric marker and at least an outer layer of the catheter shaft are formed of the same class of the polymers (e.g., polyamides) so that they are melt bondable together. In another embodiment, the polymeric markers are installed on a dissimilar class of polymeric substrate, and are retained in position by adhesion or dimensional interference. The polymer must also impart sufficient strength and ductility to the marker compound so as to facilitate its extrusion and forming into a marker, its subsequent handling and attachment to a medical device and preservation of the marker's integrity as the medical device is flexed and manipulated during use. Examples of such polymers include but are not limited to polyamide copolymers like polyether block amide (PEBAX), polyetherurethanes like PELLETHANE, polyester copolymers like HYTREL, olefin derived copolymers, natural and synthetic rubbers like silicone and SANTOPRENE, thermoplastic elastomers like KRATON and specialty polymers like EVA and ionomers, etc. as well as alloys thereof. A Shore durometer of not greater than about 63D to about 25D is preferred. The preferred polymer for use in the manufacture of a marker in accordance with the present invention is polyether block polyamide copolymer (PEBAX), with a Shore durometer of about 40D. However, other classes of polymers allowing for lower durometers may be used in the radiopaque markers, such as polyurethanes, which may provide greater flexibility.

A number of different metals are well known to be radiographically dense and can be used in a pure or alloyed form to mark medical devices so as to render them visible under fluoroscopic inspection. Commonly used metals include but are not limited to platinum, gold, iridium, palladium, rhenium and rhodium. Less expensive radiopaque agents include tungsten, tantalum, silver and tin, of which tungsten is most preferred for use in the markers of the present invention.

The control of particle size has been found to be of critical importance for achieving the desired ultra high fill ratios. While efforts to increase fill ratios have previously utilized small average particle sizes (1 micron or less) so as to minimize the ratio of particle size to as-extruded wall thickness, it has been found that higher fill percentages can be realized with the use of somewhat larger average particles sizes. It is desirable in the formulation of high fill ratio compounds to have the following attribute: 1) uniform distribution of the filler particles, and 2) continuity of the surrounding polymer matrix, and 3) sufficient spacing between filler particles so that the polymer matrix provides ductility to the bulk mixture to impart processability in both the solid and molten state.

The use of larger average particle sizes results in greater spacing between filler particles at a given percentage, thus maintaining processability during compounding and especially subsequent extrusion coating. The upper limit of average particle size is determined by the wall thickness of the coating and the degree of non-uniformity tolerable (i.e., surface defects). It has been found that a particle size distribution having an average particle size range of at least 2 microns to 10 microns and a maximum particle size of about 20 microns yields the desired fill ratio and provides for a smooth surface in the marker made therefrom.

The control of particle shape has also been found to be of critical importance for achieving the desired ultra high fill ratios. Discrete particles of equiaxed shape have been found to be especially effective, as individual particles of irregular shape, including agglomerations of multiple particles, have been found to adversely impact the surface, and thus, the maximum fill ratio that is attainable.

It has also been found that the process by which certain metal powders are produced has a profound effect on the shape of the individual particles. In the case of metallic tungsten, the powders may be formed by the reduction of powdered oxides through either "rotary," "pusher" or "atomization" processing. Of these processes, "rotary" processing has been found to yield the least desirable shape and size distribution as partial sintering causes coarse agglomerates to be formed which do not break up during compounding or extrusion and thus adversely effect the marker manufactured therefrom. Atomized powders have been reprocessed by melting and resolidifying "rotary" or "pusher" processed powders and result in generally equiaxed, discrete particles which are suitable for use in the present invention. "Pusher" processed powders are preferred due to their low cost and discrete, uniformly shaped particles.

In order for the polymer to most effectively encapsulate individual radiopaque particles, it is necessary for a low-energy interface to exist between such particles and the polymer so as to enable the polymer to "wet" the surface of the particles. The materials should have similar surface energies to be compatible. For materials which do not naturally have similar surface energies, compatibility can be promoted by generating a similar surface energy interface, i.e., a surface energy interface which is intermediate between the natural surface energies of the materials. Certain additives such as surfactants and coupling agents may serve as wetting agents and adhesion promoters for polymer/metal combinations that are not naturally compatible. It has been found that additives containing maleic anhydride grafted to a polyolefin backbone provide a significant benefit in this regard wherein materials commercially available as Lotader 8200 (having LLDPE Backbone) and Licomont AR504 (having PP backbone) were found to be particularly effective for use with tungsten/Pebax combinations. Emerging extrusions were found to be less susceptible to breakage, and the melt viscosity during compounding was lower as was manifested by a reduction in torque exerted during the extrusion process. The use of such additives allowed compounds with higher fill ratios to be successfully produced.

The inclusion of an antioxidant in the marker composition has also been found to be of benefit. Commercially available antioxidants such as Irganox B225 or Irganox 1010, have been found to minimize degradation (i.e., reduction in molecular weight) of the polymer matrix as it is exposed to the multiple heat and shear histories associated with the compounding, extrusion, and bonding processes.

The compound used for the manufacture of the marker of the present invention is preferably made by first blending the polymer resin and wetting agent, and optionally, an antioxidant such as by tumble mixing after which such blend is introduced into a twin-screw extruder via a primary feeder. The feed rate is carefully controlled in terms of mass flow rate to ensure that a precise fill ratio is achieved upon subsequent combination with the radiopaque agent. The heat that the materials are subjected as they are conveyed through the extruder causes the polymer to melt to thereby facilitate thorough homogenization of all of the ingredients. The radiopaque agent powder, selected for its uniform particle shape and controlled particle size distribution as described above is subsequently introduced into the melt stream via a secondary feeder, again at a carefully controlled mass flow rate so as to achieve the target fill ratio. The solid powder, molten polymer and additives are homogenized as they are conveyed downstream and discharged through a die as molten strands which are cooled in water and subsequently pelletized. The preferred extrusion equipment employs two independent feeders as introduction of all components through a single primary feeder would require significantly higher machine torques and result in excessive screw and barrel wear. The powder feeder is preferentially operated in tandem with a sidefeeder device, which in turn conveys the powder through a sealed main barrel port directly into the melt stream. A preferred composition comprises a fill ratio of at least 90.8 weight percent of tungsten (H.C. Starck's Kulite HC600s, HC180s and KMP-103JP) to Pebax 40D. A maleic anhydride source in the form of Licomont AR504 is initially added to the polymer resin at the rate of approximately 3 pphr while an antioxidant in the form of Ciba Geigy Irganox B225 at the rate of approximately 2 pphr (parts per hundred relative to the resin). The temperature to which materials are subjected to in the extruder is about 221° C.

Once the marker material has been compounded, the marker can be fabricated in suitable dimensions by an extrusion coating process. While free extrusion is possible, this method is problematic due to the high fill ratios of the polymeric materials. Extrusion onto a continuous length of beading has been found to lend the necessary support for the molten extrudate to prevent breakage. The support beading may take the form of a disposable, round mandrel made of PTFE (Teflon) coated stainless steel wire or other heat resistant material that does not readily bond to the extrudate. By additionally limiting the area draw down ratio (ADDR) to below 10:1 the tungsten-laden melt can successfully be drawn to size by an extrusion puller. The beading provides the added benefit of fixing the inner diameter and improving overall dimensional stability of the final tungsten/polymer coating. Extrusions of a 91.3 weight percent fill ratio tungsten/Pebax composition described above over 0.0215" diameter PTFE beading were successfully drawn down to a wall thickness of 0.0025" to yield a marker properly sized for attachment to for example a 0.022" diameter inner member of balloon catheter. Also, extrusion coatings of 91% compound over 0.007" teflon coated stainless steel wire were successfully drawn down to single wall thicknesses of 0.002" to make guidewire coatings.

In one embodiment, once the extrudate has cooled, the extrusion is simply cut to the desired lengths (e.g., 1 to 1.5 mm) of the individual markers, such as with the use of a razor blade and reticle, preferably with the beading still in place to provide support during cutting. The beading remnant is subsequently ejected and the marker is slipped onto a medical device or a particular component thereof. In one embodiment, a segment of the extrudate is hot die necked with the beading inside to resize the outer diameter and wall thickness of the extrudate prior to cutting into individual markers. For example, an extrudate, having an inner diameter of about 0.0215±0.0005 inches and an outer diameter of about 0.0275±0.001 inches, is hot die necked to an outer diameter of about 0.0265 inches to produce a double wall thickness of about 0.005±0.0005 inches. To minimize part to part variability in double wall thickness, the actual hot die size may be selected based upon the actual beading diameter prior to hot die necking.

Finally, the marker is attached to the underlying substrate, preferably with the use of heat shrink tubing and a heat source (hot air, laser, etc.) wherein the heat (~171-210° C.) simultaneously causes the marker to melt and the heat shrink tubing to exert a compressive force on the underlying molten material. To prevent extensive dimensional changes (e.g., thinning) of the polymeric marker, the temperatures used are below the melting temperature, thereby relying on heat and pressure to soften the marker and generate an adhesive bond with the underlying substrate. For markers formed of PEBAX 40D, the temperature used is about 120-135° C. Heat bonding a marker onto an underlying component provides the added benefit of slightly tapering the edges of the marker to reduce the likelihood of catching an edge and either damaging the marker or the medical device during assembly or handling of the medical device.

A marker formed as per the above described compounding, fabricating and assembling processes, having a fill ratio of 91.3 weight percent (36.4 volume percent) with a wall thickness of 0.0025" has been shown to have dramatically more radiopacity than commercially available 80 weight percent compounds and comparable to the radiopacity of 0.00125" thick conventional Platinum/10% Iridium markers. The radiopacity is a function of the total volume of radiopaque material present in the marker (i.e., the product of the volume % and the volume of the marker). In a presently preferred embodiment, the marker is about 1.5 mm long and has a double wall thickness of about 0.0045 to about 0.0055 inches and a fill ratio of about 90.8 to about 93.2 weight percent of tungsten, which provides a volume of radiopaque material substantially equal to the volume of Platinum/10% Iridium in a 1.0 mm long, 0.0025 inches thick (double wall) conventional Platinum/Iridium marker band. Preferably, the volume of radiopaque material is not less than about 30%, and the double wall thickness of the marker is at least about 0.004 inches, to provide sufficient radiopacity. However, as discussed above, the ability to increase the volume of the marker by increasing the wall thickness of the marker is limited by the resulting increase in profile and stiffness. In a presently preferred embodiment, the double wall thickness of the marker is not greater than about 0.006 inches.

FIG. 1 illustrates two radiopaque markers 12 attached to the inner member 14 of a balloon catheter 16. During assembly of the catheter 16, the markers are attached to the inner member prior to the positioning of the inner member within the balloon 18 and attachment thereto at 20. Fluoroscopic illumination of the device allows the nonradiopaque balloon to be positioned relative to a lesion by virtue of the visibility of the radiopaque markers under fluoroscopy and their known positions relative to the balloon. The balloon catheter 16 generally comprises an elongated shaft having an inflation lumen and a guidewire lumen, and balloon 18 with a proximal end and distal end sealingly secured to a distal section of the shaft and an interior in fluid communication with the inflation lumen. The shaft typically comprises an outer tubular member defining the inflation lumen, and the inner tubular member 14 extending within at least a portion of the inflation lumen and defining the guidewire lumen.

Figure 2:
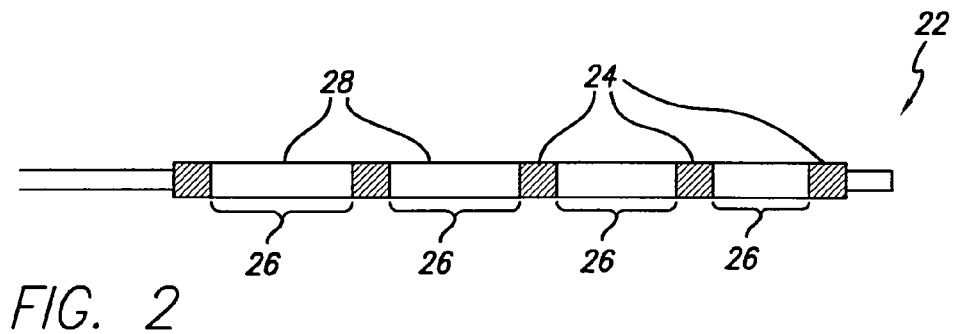
FIG. 2 is an enlarged side view of radiopaque markers of the present invention attached to a guidewire in a preferred configuration.

FIG. 2 illustrates a preferred embodiment of a guidewire with a measurement feature 22 wherein a series of radiopaque markers 24 are attached to the core member of the guidewire 24 at preselected separation distances 26 to allow the device to be used as a type of ruler to measure the size of a lesion. The separation between adjacent markers may be controlled by the use of radiotransparent tubular spacers 28 that are similarly adhered to the underlying guidewire. Upon assembly of the radiopaque markers and the radiotransparent spacers onto at least a distal section of the guidewire core member, heat shrink tubing of sufficient length is slipped over the entire section of guidewire and heated to the appropriate temperature to cause both the markers as well as the spacers to become adhered to the guidewire core member.

Figure 3:
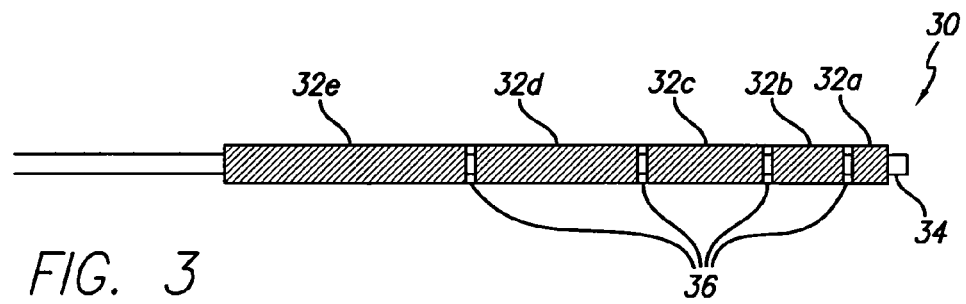
FIG. 3 is an enlarged side view of the radiopaque markers of the present invention attached to a guidewire in an alternatively preferred configuration.

FIG. 3 illustrates an alternatively preferred embodiment of a guidewire with a measurement feature 30 wherein an equally spaced series of differently sized radiopaque markers 32a-e are attached to the core member of guidewire 34 to allow the device to be used to gauge the size of a lesion. The separation between adjacent markers may be controlled by the use of radiotransparent tubular spacers 36 that are similarly adhered to the underlying guidewire. Upon assembly of the radiopaque markers and the radiotransparent spacers onto the guidewire core member, heat shrink tubing of sufficient length is slipped over the entire section of guidewire and heated to the appropriate temperature to cause both the markers as well as the spacers to become adhered to the guidewire core member.

While a particular form of the invention has been described, it will be apparent to those skilled in the art that various modifications can be made without departing from the spirit and scope of the invention. More specifically, a variety of different polymers and radiopaque agents can be compounded using the appropriate wetting agent, markers of different shape and dimensions can be formed and the markers can be attached to any of a variety of medical devices that can benefit from being radiopaquely marked. Accordingly, it is not intended that the invention be limited except by the appended claims.

What is claimed is:

1. An intraluminal medical device, comprising an elongated shaft or core member having a radiopaque marker circular band secured to a surface of the shaft or core member, and the radiopaque marker is formed of a compounded polymer mixture comprising:
 a) a polymer;
 b) radiopaque particles having an average diameter of at least about 2 microns and a maximum diameter of about 20 microns, the radiopaque particles comprising about 90.8 to about 93.2 weight percent of the compounded polymer mixture; and
 c) a wetting agent for facilitating encapsulation of said particles by said polymer, and wherein the marker band has a radiopacity that is substantially constant along the length of the marker band, and a double wall thickness that varies by less than 0.001 inches along the entire length of the marker band.

2. The intraluminal medical device of claim 1 wherein the double wall thickness of the radiopaque marker is about 0.004 to about 0.006 inches.

3. The intraluminal medical device of claim 1 wherein the double wall thickness of the radiopaque marker varies by about ±0.0005 inches along the entire length of the marker band.

4. The intraluminal medical device of claim 1 wherein the radiopaque marker is secured to the shaft or core member with an adhesive.

\* \* \* \* \*